US006991704B2

(12) United States Patent
Broadbent

(10) Patent No.: US 6,991,704 B2
(45) Date of Patent: Jan. 31, 2006

(54) HEATING OF MICROTITRE WELL PLATES IN CENTRIFUGAL EVAPORATORS

(75) Inventor: Graham Broadbent, Suffolk (GB)

(73) Assignee: Genevac Limited, Ipswich (GB)

( * ) Notice: Subject to any disclaimer, the term of this patent is extended or adjusted under 35 U.S.C. 154(b) by 22 days.

(21) Appl. No.: 10/311,450

(22) PCT Filed: Apr. 24, 2002

(86) PCT No.: PCT/GB02/01874

§ 371 (c)(1),
(2), (4) Date: Jun. 16, 2003

(87) PCT Pub. No.: WO02/087765

PCT Pub. Date: Nov. 7, 2002

(65) Prior Publication Data

US 2004/0026046 A1 Feb. 12, 2004

(30) Foreign Application Priority Data

Apr. 28, 2001 (GB) .................................. 0110447

(51) Int. Cl.
*B01D 1/00* (2006.01)
*B04B 5/00* (2006.01)
*H01L 23/552* (2006.01)

(52) U.S. Cl. .............................. 159/6.1; 159/DIG. 15; 159/DIG. 16; 494/20; 257/659

(58) Field of Classification Search ................. 159/6.1, 159/DIG. 15, DIG. 16; 494/20, 85; 335/285; 257/659, E23.114; 436/807

See application file for complete search history.

(56) References Cited

U.S. PATENT DOCUMENTS 4,913,696 A    4/1990  Romanauskas et al.

(Continued)

FOREIGN PATENT DOCUMENTS

GB          2334688 A      9/1999

(Continued)

OTHER PUBLICATIONS

The Bergquist Company, "Sil-Pad Selection Guide 2002".

*Primary Examiner*—Virginia Manoharan
(74) *Attorney, Agent, or Firm*—Barnes & Thornburg LLP

(57) ABSTRACT

A centrifugal evaporator is described having internally of a chamber a source of IR radiation which directs energy towards a sample support platform on which a microtitre plate is mounted in use, for rotation within the chamber. The wells of the microtitre plate will normally contain liquid samples which are to be evaporated whilst subjected to heat from the IR source and centrifugal force from the rotation of the platform. The swing characteristic of the latter allows the plate to be mounted and demounted with the plate generally horizontal, but as the support platform is rotated, it swings up through approximately 90° so that the wells are now substantially horizontal and the plate is now substantially vertical, so that centrifugal force pins the liquid at the bottom of the wells. A layer of thermally conductive compliant material is located between the underside of the wells of the microtitre plate and the support platform, such that during centrifuging the underside of the wells become embedded in the compliant material, to increase the area of contact between the wells and the material to increase heat transfer therebetween. Since the wells may be at least in part translucent or transparent, the compliant material is selected as being a poor conductor of electromagnetic radiation in the range 200–3000 nm.

11 Claims, 4 Drawing Sheets

U.S. PATENT DOCUMENTS

Figure 1:
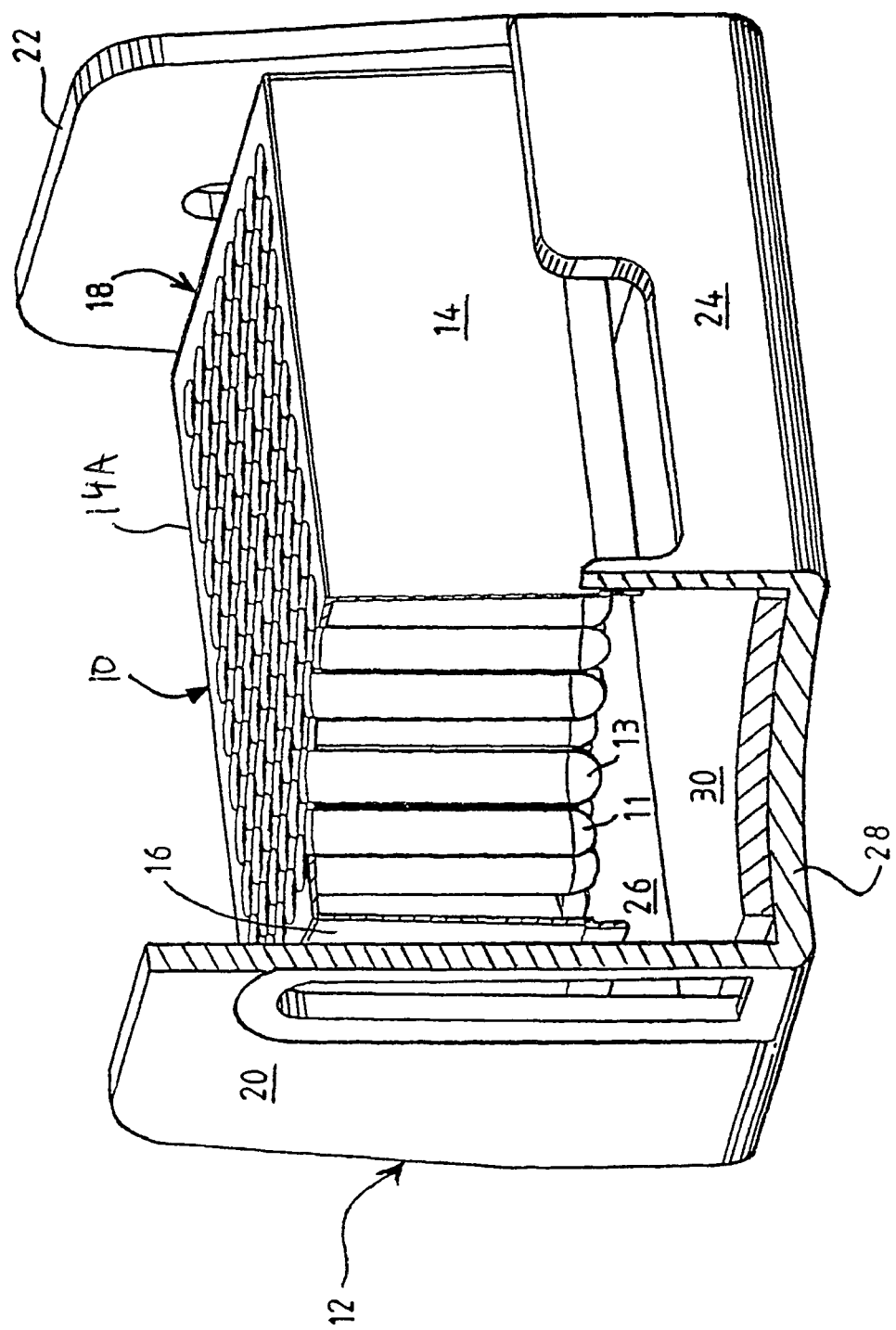

| | | |
|---|---|---|
| 5,175,613 A | 12/1992 | Barker |
| 5,325,265 A * | 6/1994 | Turlik et al. ................. 361/702 |
| 6,045,760 A | 4/2000 | Aizawa et al. |
| 6,605,474 B1 * | 8/2003 | Cole ........................... 436/177 |

FOREIGN PATENT DOCUMENTS

| | | |
|---|---|---|
| WO | WO 92-15930 A1 | 9/1992 |
| WO | WO 01/04600 A1 | 1/2001 |

* cited by examiner

HEATING OF MICROTITRE WELL PLATES IN CENTRIFUGAL EVAPORATORS

FIELD OF INVENTION

This invention concerns centrifugal evaporators and processes for evaporation primarily for separating volatile components from less volatile components of liquid mixtures, typically volatile solvents in liquid mixtures.

BACKGROUND TO THE INVENTION

In the preparation of pharmaceuticals and drugs it is a common requirement to separate unwanted volatile solvent components from less volatile materials and one technique which has been developed involves centrifuging the mixture whilst simultaneously evacuating the chamber containing the centrifuged material so as to draw off from the mixture the more volatile component and leave the less volatile material behind. Thus chemists and biologists frequently need to remove liquids in which the solid matter in which they are interested is dissolved or suspended. The solid matter may be potential new drugs, biological samples or other materials. They are frequently sensitive to heat, so that the mixture cannot be boiled off at atmospheric pressure because this would involve excessively high temperatures. Boiling, or evaporation under vacuum is often the preferred process because this can be done at low temperatures which do not harm the samples. If samples in liquids are exposed to vacuum they tend to boil vigorously and this activity can lead to liquid containing valuable sample material being spilled or lost, or worse, to cross-contamination of samples which may have been expensively purified.

It is therefore well known to spin such samples in a closed vacuum chamber so as to subject them to rotation generated centrifugal forces which suppress the spitting or frothing of the liquid while it is boiling under vacuum. This process is known as Centrifugal Evaporation, or Concentration.

If such a Centrifugal Evaporator is to achieve rapid evaporation of solvents it is necessary to heat the samples to provide the energy necessary to sustain evaporation. One well known method of heating is by the use of infra red radiation from lamps located in the wall of the vacuum chamber. Once the solvent within the receptacle is boiling, the rate of evaporation is governed only by the rate of heat input to the solvent.

One known method of operation is to locate the receptacle in which the sample is contained in a holder that will allow infra red radiation from the lamps to heat the solvent in the receptacle directly. This method has the disadvantage that when the solvent in the receptacle is all evaporated, the temperature of the remaining solid compounds cannot be controlled and will increase very rapidly unless the infra red lamps are turned off. Many of the biological compounds that are regularly dried by these evaporators are highly temperature sensitive. A further disadvantage is that the solids while in solution and when dry are subjected to possibly damaging levels of radiation in wavelengths from ultra violet through visible to infra red. With the development of genetic testing using Oligonucleotide Probes it is becoming increasingly common for such probes to contain a "marker", and these markers are often sensitive to radiation and can therefore be damaged by a broad range of wavelengths including the range from ultra violet through visible to infra red.

An alternative known method aimed at overcoming the problem of temperature control highlighted above is to locate the receptacle in one or more solid aluminium blocks. In this case the block will protect the dried compounds from direct infra red radiation. The radiation from the lamps will heat the block and in turn heat will be transferred to the solvent by conduction between the sample receptacle and the aluminium block. This method gives good temperature control of the samples but has the disadvantage of slow evaporation with some formats of sample receptacle. Receptacles such as Microtitre plates give particularly slow evaporation when conduction is used to transfer the heat required for evaporation into the plate.

It has been proposed in GB 2,334,688 to provide a platform on a tray on which a microtitre well plate is located to engage a recessed underside of the microtitre plate which will otherwise be spaced from the surface of the tray, to improve heat transfer between tray and plate. However the provision of such a platform has not been found to satisfactorily increase heat transfer in practice due to the shape of the ends of the wells.

Damage to the samples by UV, visible and infra red radiation can be reduced by not using infra red lamps at all, but this has the disadvantage of increasing the length of time required for evaporation.

An alternative approach is to use a filter positioned between the IR source and the aperture into the chamber. Such filters are practical in filtering out harmful radiation in the range of wavelengths from 200 nm through to 600 nm but above this figure such filters start to significantly reduce the energy transfer from the source into the evaporation chamber.

It is an object of the present invention to provide a method and apparatus which will allow use of infra red lamps to speed the evaporation of sample solvents especially when contained within wells in microtitre well-plates, or in other sample holders having external undersides which are not substantially flat.

SUMMARY OF THE INVENTION

According to one aspect of the present invention there is provided a centrifugal evaporator in which a source of infra red radiation directs heat energy towards a sample support therein, to heat the support and in turn evaporate liquid material in a sample holder therein, the support including a base and sides for retaining the holder whilst it is subjected to heat and centrifugal force during operation of the evaporator, characterised in that a cushion of thermally conductive compliant material is sandwiched between the holder and the support so that under centrifugal loading the holder becomes embedded into the compliant material, thereby increasing the area of contact between the holder and the compliant material during centifuging, and thereby increasing the rate of transfer of heat from the support to the holder and therefore the liquid material therein.

Typically the support surrounds the holder and is constructed from material which is impervious to electromagnetic radiation having wavelengths in the range 200–3000 nm, but is absorbent of infra red radiation so that its temperature is raised by the impingement of infra red radiation thereon.

If the support is transparent to, or contains openings through which electromagnetic radiation having wavelengths in the range 200–3000 nm can reach the compliant material, preferably the latter is selected or adapted so as to be substantially impervious to electromagnetic radiation having wavelengths in that range.

In one arrangement in which primarily only the base of the support is subjected to infra red radiation the compliant material may be sandwiched only between a lower end of the sample holder and the base of the support.

According to another aspect of the invention there is provided a centrifugal evaporator which comprises a sealable enclosure, having at least one swing support rotatable therein, the support having a base and sides and adapted to receive and support at least one microtitre well-plate therein, and an infra red radiation source which is operated during the centrifuging to direct radiation towards the underside of the base of the support, to heat the base and in turn liquid sample material in the wells of the microtitre well plate characterised by a layer of compliant heat conducting material in the support on which the underside of the well-plate rests when located therein, so that compliant material is sandwiched between the undersides of the wells and the base of the support, wherein the compliance of the material is selected such that during the centrifuging operation, the wells become partially embedded under centrifugal force in the compliant material, thereby increasing the area of the compliant material in contact with the wells and increasing the rate of heat transfer therebetween.

Where the well-plate comprises a housing having external peripheral walls defining a volume within which the wells extend to a lesser extent than the height of the walls, so that if placed on a flat surface, the bottoms of the wells are spaced from the surface by a gap of size h, then the thickness of the layer of compliant material is preferably greater than h so that with the layer of compliant material on a flat surface and with the wells resting thereon, the lower edges of the well-plate housing are spaced from the said surface. If the layer is wholly contained within the housing wall, its thickness needs to be greater than h, but in any event its compliance is selected so that it is not stressed beyond its elastic limit during, and will recover its original shape after centrifuging.

Typically the microtitre plate is formed from moulded plastics material and at least the base of each well is translucent or transparent to electromagnetic radiation having wavelengths in the range 200–3000 nm, and in this event, if the support is not impervious to electromagnetic radiation having wavelengths in the range 200–3000 nm, the compliant material is preferably selected or adapted to be a poor transmitter of electromagnetic radiation in that wavelength range, so as to serve as a shield to prevent radiation of those wavelengths from reaching the wells and the sample material therein.

The cushion or layer of compliant material is preferably a fibre reinforced alumina-filled silicon gel; a polyurethane; or a nitrile composition.

The invention also lies in a heat transmitting cushion, which is compliant and is adapted to be fitted between the underside of a microtitre well-plate and a support plate therefor in a centrifugal evaporator, which platform is heated by infra red radiation during centrifuging, wherein heat is conveyed to the wells through the platform and the cushion of compliant material, and the compliance of the material is such as to permit intrusion by the lower ends of the wells into the cushion material when the well-plate is acted on by centrifugal forces during rotation, thereby to increase the area of the cushion material in contact with the wells and increase the rate of heat transfer to the wells during an evaporative centrifuging process.

The heat transmitting cushion is preferably formed from a fibre reinforced alumina-filled silicon gel; a polyurethane; or a nitrile composition.

The heat transmitting cushion preferably absorbs infra red radiation and preferably is, or is adapted to be, substantially impervious to electromagnetic radiation having wavelengths in the range 200–3000 nm.

The invention also lies in a method of locating a microtitre well plate in a rotatable support in a centrifugal evaporator in which a source of infra red radiation is directed towards the support during centrifuging to provide heat to evaporate sample material in the wells, and wherein relative sliding movement is possible between the plate and the walls of the support, comprising the step of inserting a cushion of compliant thermally conductive material between the underside of at least the wells and the support, so that at least the lower ends of the wells are supported thereon when the well plate is located in the support, and causing the lower ends of the wells to sink into the cushion under centrifugal force during centrifuging to increase the area of material in contact with the wells, and increase the rate of transfer of heat to the wells from the cushion material, to assist in heating and evaporating the liquid material in the wells.

Typically the well plate comprises a generally rectilinear housing having an outside wall, and the wells extend internally of the housing generally parallel to the outside wall to a depth which is less than the height of the wall, so that when the housing is stood on a flat surface there is a gap between the bottoms of the wells and the surface. In this event the cushion may be selected to have an uncompressed thickness which is in excess of the said gap and to be otherwise dimensioned so as to wholly fit within the housing wall, so that it becomes compressed as the well plate housing is pushed in a downward manner towards the said surface. Downward movement is limited to that permitted by the clearance between the housing wall and the said surface.

In an alternative method the area of the cushion may be greater than the area bounded by the well-plate housing wall, in which event the lower edge of the housing wall also will be pushed into the cushion in addition to the lower ends of the wells, under centrifugal force.

The cushion is preferably made from a fibre reinforced alumina-filled silicon gel; a ployurethane; or a material having a nitrile composition.

Figure 2:
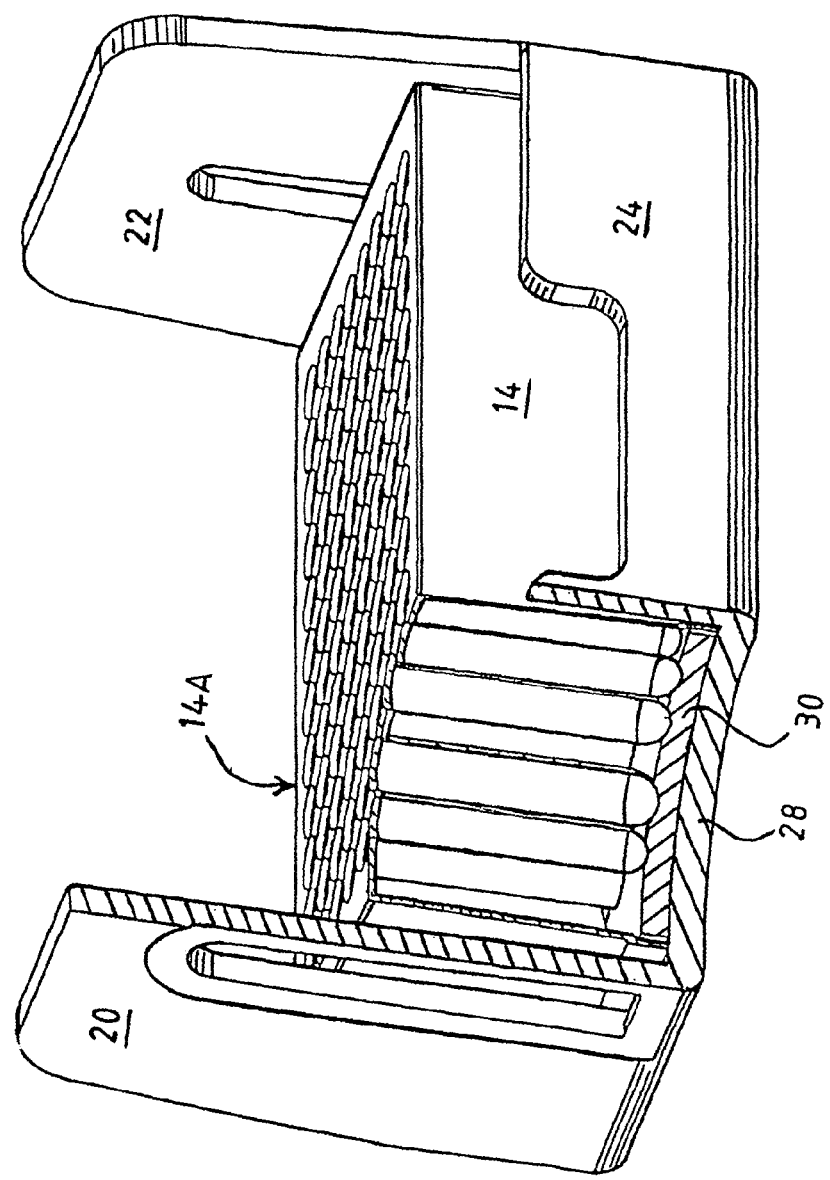
Figure 3:
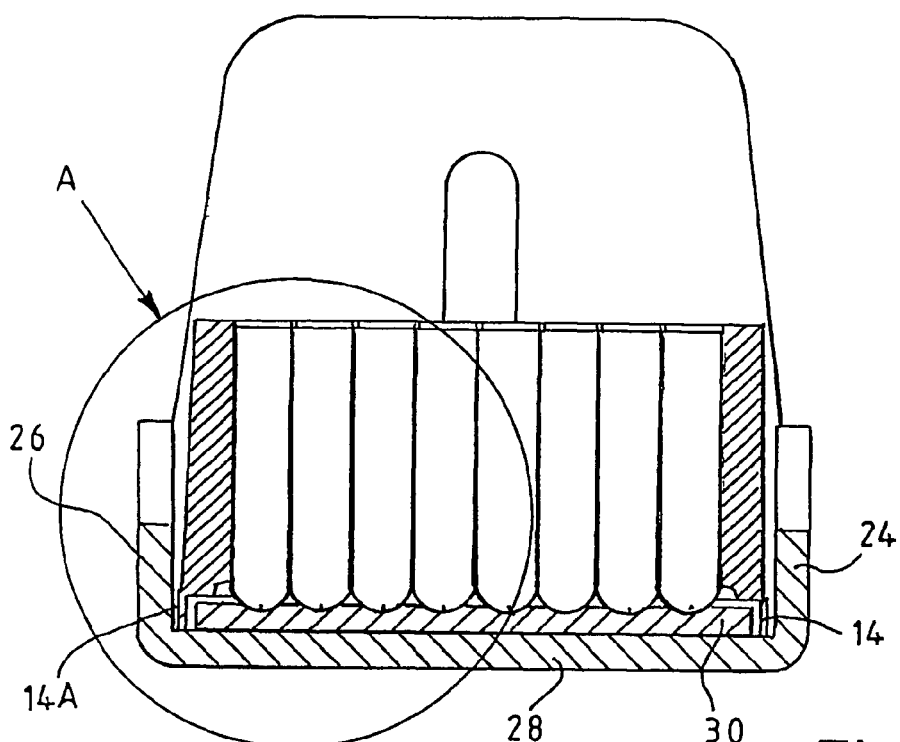
Figure 4:
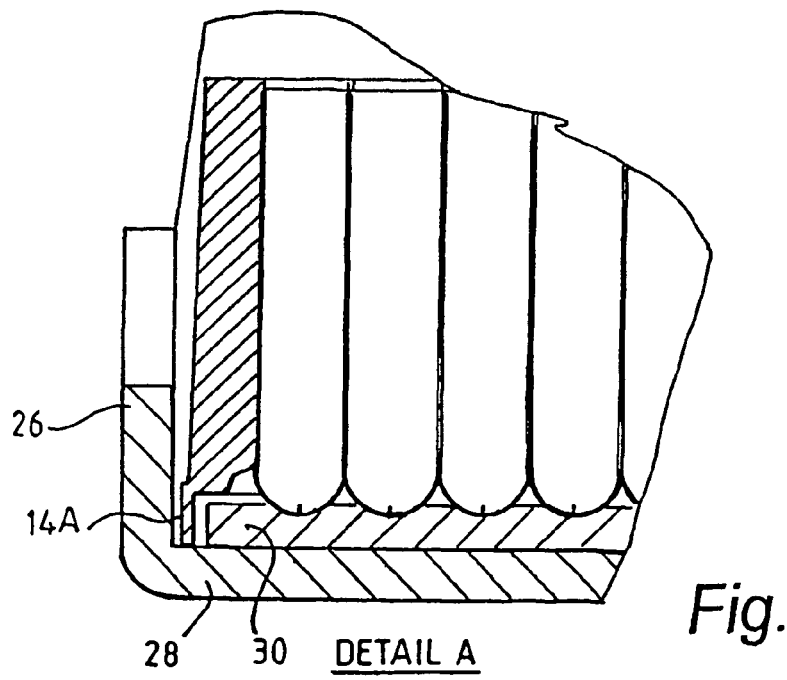
Figure 5:
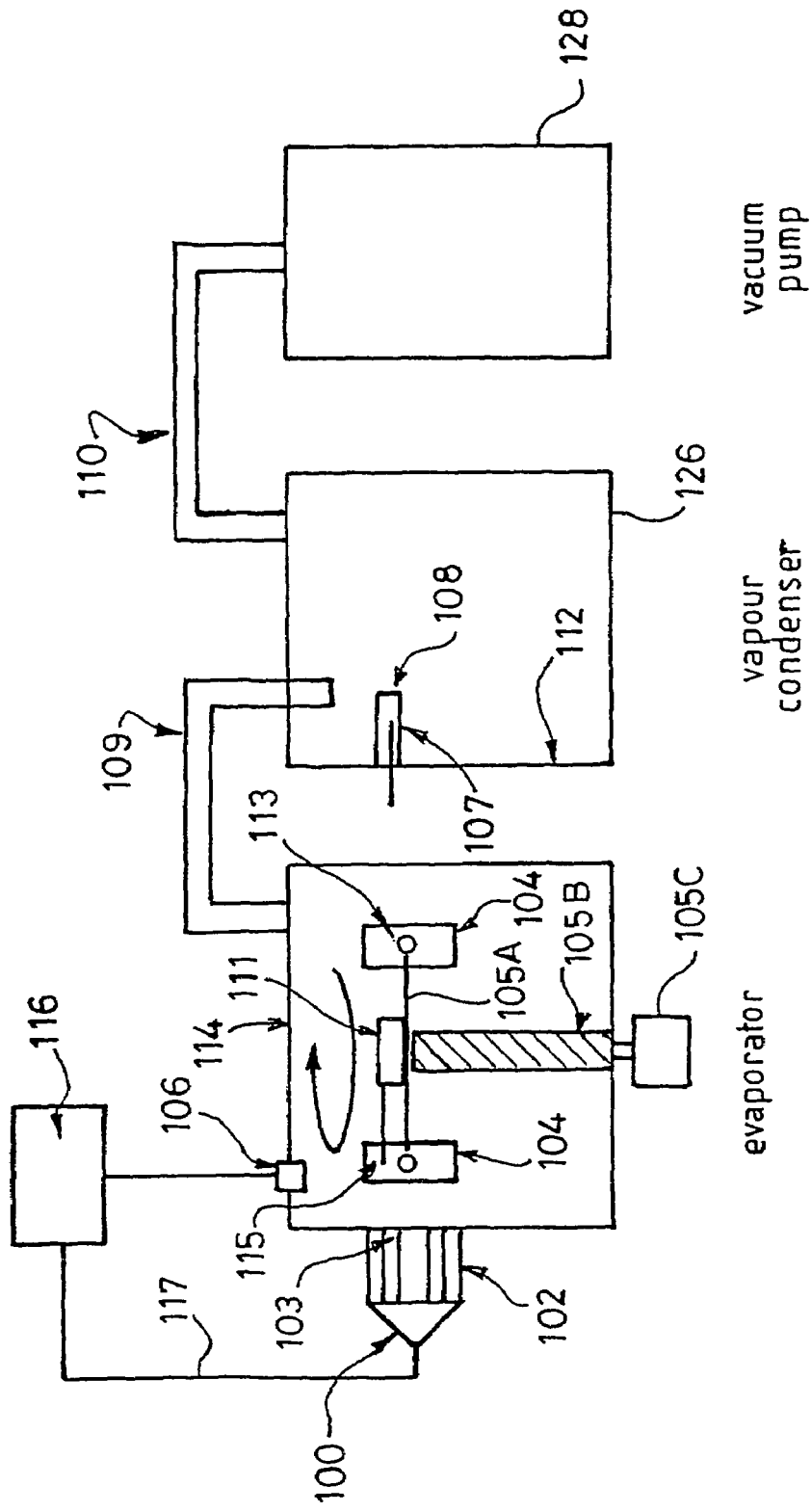

The invention will now be described by way of example with reference to the accompanying drawings in which:

FIG. 1 is a perspective view, partly cutaway, of a swinging sample support in which a microtitre well-plate is located prior to centrifuging in a centrifugal evaporator, FIG. 2 is a similar view, again partly cutaway, in which the well plate is shown at the bottom of the support, with the wells embedded in a cushion of compliant material located in the support, FIG. 3 is an end view in cross section of the arrangement shown in FIG. 2, FIG. 4 is a similar view, to a larger scale, of the cross section of FIG. 3, and FIG. 5 is a schematic diagram of a centrifugal evaporator.

In FIGS. 1 to 4 of the drawings a generally rectilinear microtitre well plate housing 10 is shown fitted in a swing-support 12 which is mounted in use on a rotor assembly (not shown) within a sealable chamber (compare chamber 114, FIG. 5) of a centrifugal evaporator. Evaporation is achieved by sealing the chamber and reducing the pressure in the chamber until it is below the boiling point of the liquids in the wells so that the liquid (solvent) material is boiled away leaving a solid residue in the base of the wells. In known manner (as shown in FIG. 5) the rotor and the well plate are rotated at high speed within the chamber as the pressure is reduced so as to impart centrifugal force to the liquid material in the wells, thereby to reduce the tendency for the liquid material to boil vigorously and bump and spit. In this way the boiling process can be controlled inter alia to prevent cross contamination of the materials in the wells. The swinging characteristic of the support allows the well-plate to swing up from a generally vertical mode (in which the wells are therefore vertical), so as to occupy a generally horizontal mode in which the wells are therefore also generally horizontal with their closed ends outermost, so that centrifugal force pins the contents of each well at its closed end.

Control of pressure and speed of rotation for difficult mixtures of solvents is described in WO99/33538 published Jul. 8, 1999.

The wells can be likened to a matrix of small diameter test tubes (see 11, 13 in FIG. 1), since the lower end of each well is semi-cylindrical like that of a test tube. However these lower ends of the wells are kept clear of any flat surface on which the well plate housing is located by the side walls of the housing such as 14, 14A, 16 and 18 which extend to a greater extent than do the wells.

As shown in FIG. 1, housing 10 is shown at the upper end of the support 12 with the ends 16, 18 of the housing between the parallel end walls 20, 22 of the support 12.

The support includes side walls 24, 26 and a base 28 and as shown the nearside corners of the support 12 and the well plate housing 10 are cut-away.

FIG. 1 also shows a layer of compliant thermally transmittive material 30 located on the base 28 of the support to form a cushion between the well-plate and the base 28.

When the well plate housing 10 is lowered to the bottom of the support, the bottoms of the wells (such as 11, 13) rest on the surface of the cushion 30 as shown in FIG. 2, and with rotation, so that the support 12 swings through 90° in known manner, the wells now become generally horizontal, and the centrifugal forces acting on the well plate housing 10 cause the bottoms of the wells to press into the cushion 30 as best seen in the cross-section views of FIGS. 3 and 4.

The dimensions of the cushion layer 30 may be such that it is wholly accommodated within the side walls 20–26 so that downward movement of the latter is not impeded by the compliant material, which is thereby only penetrated by the lower ends of the wells such as 11, 13. In this event the depth of penetration of the wells into the cushion is either limited by the engagement of the lower edges of the end and side walls 14, 14A, 16 and 18 of the housing 10 with the base 28, or by selecting the thickness and compliance of the material forming the cushion, so that the depth to which the wells can be pushed into the cushion during rotation will not cause the well-plate walls 14, 14A, 16 and 18 to reach the base 28.

If the support 12 is formed from material which is transparent to infra-red radiation or includes openings which allow radiation to pass through the base 28, radiation emitted by the infra red source, which may degrade or otherwise alter the characteristics of liquid materials in the wells, can also reach the wells. To this end the compliant material selected for the cushion 30 should be (or should be adapted to be) substantially opaque to wavelengths of electromagnetic radiation in the range 200–3000 nm. However, infra red radiation incident thereon after passing through transparent regions of (or openings in) the support base 28 will still cause the cushion to heat up and thereby in turn heat up the wells such as 11, 13 etc., and sample material therein.

The cushion 30 may be self-adhesive on the face which is to make contact with the base 28 to secure it in place.

FIG. 5 shows diagrammatically a centrifugal evaporator, in which samples in are contained in wells in microtitre well plates 104 containing numerous sample wells (not shown), typically 96 or more, and commonly referred to as deep well plates.

When the sample holder rotor 105A and shaft 105B rotates, driven by a motor 105C, which may be inside but more usually external to the chamber 114, the well-plates swing out to the position illustrated in which the sample wells are horizontal, under the influence of centrifugal force.

The well-plates are connected to pivots 113 and the plates are held with the wells vertical for loading into a stationary evaporator. Vacuum is then applied to the evaporator chamber 114 via pipe 109 from the vapour condenser which in turn is pumped via pipe 110 by the vacuum pump 128.

Heat is applied to the samples in the wells in the rotating well-plates 104 by a high temperature infra-red radiation source 101. Radiant heat energy 102 passes through a window of heat-transparent material such as quartz which is sealed into the wall of the vacuum chamber 114, and reaches the well-plates as illustrated.

A temperature sensor or probe 115 is placed in one of the sample wells, or otherwise placed in close proximity to the wells in one of the well-plates, and is connected to transmitter 111 which transmits signals corresponding to the sample temperature to an aerial and feedthrough 106 inside and extending through the chamber wall, and which is connected to a receiver and decoder 116. This includes data processing and computing facilities as required, and indicates the sample temperature by a display (not shown) and, if required, can be programmed to generate electrical signals to control the operation of the heater to increase or decrease the heat energy to keep the samples at desired temperatures during the process. Such control signals are supplied to the heater via path 117.

Where the sample holder is a deep-well microtitre plate, typically containing 96 wells, the plate is mounted in a swinging support that is carried on swivel pins (not shown) so that when the well-plate is initially loaded, with the rotor 105A stationary, the open ends of the wells face upwards. However as soon as rotor 105A is rotated at a sufficient speed, the support and well-plate 104 swings into a position in which the wells are generally horizontal, as is in fact shown in FIG. 5.

The heater power is controlled by measuring sample and/or chamber pressure and taking appropriate steps to raise or lower the heater power. Thus at the start of the process a high heat input is required but as the samples approach dryness the evaporation rate will reduce and the sample temperature will start to rise so that the heat input must be reduced to avoid overheating the samples. When the samples are dry, the heating must be discontinued.

A vapour condenser is shown at 126 in FIG. 5. These devices are useful in centrifugal evaporation equipment to increase pumping speed for the liquid being evaporated and to protect the vacuum pump shown at 128 from vapours which might impair its efficiency.

A centrifugal evaporator is described in GB Patent Specification 2,334,688 especially in relation to FIG. 1 of that Specification. However the present invention represents an advance over the proposal contained in that earlier Patent Specification, which describes a microtitre plate mounted on a tray having an upstanding region defining a platform adapted to engage the recessed underside of a microtitre plate located thereon and which would otherwise be spaced from the surface of the tray, to improve heat transfer between the tray and the plate. In the present invention the convex undersides of the wells are pressed into the compliant cushion material so as to increase the area in contact and this greatly increases heat transfer as compared with a platform merely engaging the recessed underside of the well plate. Furthermore by selecting a material for the cushion which does not transmit radiation having a wavelength in the range 200–3000 nm, but will absorb such radiation and thereby rise in temperature, so damaging radiation from an IR heating source can be prevented from reaching the contents of the wells should the tray not be 100% impervious to any such damaging radiation, or includes openings through which such radiation could otherwise penetrate to the wells.

What is claimed is:

1. A centrifugal evaporator comprising a sealable enclosure, means for applying suction to the enclosure, a sample support rotatably mounted therein and carrying a sample holder for containing a liquid sample material, a source of infrared radiation for directing heat energy towards the support to heat the support and in turn evaporate the liquid material in the holder, the support including a base and sides for retaining the holder while it is subject to heat and centrifugal force during operation of the evaporator, wherein a cushion of thermally conductive compliant material is located between the holder and the support so that under centrifugal loading the holder presses against the compliant material and becomes partially embedded therein, thereby increasing the area of contact between the holder and the compliant material during centrifuging, and increasing the rate of transfer of heat from the support to the holder and thus to the liquid sample material in the holder.

2. A centrifugal evaporator as claimed in claim 1 wherein the support surrounds the holder and is constructed from material which is impervious to electromagnetic radiation having wavelengths in the range 200–3000 nm, but is absorbent of infra red radiation so that its temperature is raised by the impingement of infra red radiation thereon.

3. A centrifugal evaporator as claimed in claim 1 wherein the support is transparent to, or contains openings through which electromagnetic radiation having wavelengths in the range 200–3000 nm can reach the compliant material, and the latter is selected so as to be substantially impervious to electromagnetic radiation having wavelengths in that range.

4. A centrifugal evaporator as claimed in claim 1 wherein only the base of the support is subjected to infra red radiation and the compliant material is sandwiched only between a lower end of the sample holder and the base of the support.

5. A centrifugal evaporator according to claim 1 wherein the compliance of the material is selected so that the force exerted thereon during the centrifuging process does not stress the material beyond its elastic limit, so that it will recover its normal shape after use.

6. A centrifugal evaporator which comprises a sealable enclosure, means for applying suction to the enclosure, at least one swing support rotatable therein and having a base and sides and to receive and support at least one microtitre well-plate therein, and an infra red radiation source which is operated during centrifuging to direct radiation towards the underside of the base of the support to heat the base and in turn evaporate liquid sample material in the wells of the well-plate, wherein a layer of compliant heat conducting material is provided in the support on which the underside of the well-plate rests when located therein, so that the compliant material is sandwiched between the undersides of the wells and the base of the support, and wherein the compliance of the material is selected such that during the centrifuging operation, the wells are pressed against and become partially embedded under centrifugal force in the compliant material, thereby increasing the area of the compliant material in contact with the wells and increasing the rate of heat transfer therebetween.

7. A centrifugal evaporator as claimed in claim 6 wherein the well-plate comprises a housing having external peripheral walls defining a volume within which the wells extend to a lesser extent than the height of the walls, so that the undersides of the wells are spaced from a plane containing the lower edge of the peripheral walls of the housing by a gap h.

8. A centrifugal evaporator as claimed in claim 7 wherein the dimensions of the layer of compliant material are such that it is wholly contained within the external peripheral walls of the housing and the thickness of said layer is greater than h so that with the layer of compliant material on a flat surface and with the wells resting thereon, the lower edges of the well-plate housing are spaced from the said surface.

9. A centrifugal evaporator according to claim 6 wherein the microtitre plate is formed from moulded plastics material and at least the base of each well is translucent or transparent to electromagnetic radiation having wavelengths in the range 200–3000 nm.

10. A centrifugal evaporator according to claim 9 wherein the support is not impervious to electromagnetic radiation having wavelengths in the range 200–3000 nm and the compliant material is selected or adapted to be a poor transmitter of electromagnetic radiation in that wavelength range, so as to serve as a shield to prevent radiation of those wavelengths from reaching the holder and the sample material.

11. A centrifugal evaporator according to claim 6 wherein the compliant material is a fibre reinforced alumina-filled silicon gel; a polyurethane; or a nitrile composition.

* * * * *